(12) United States Patent
Wei et al.

(10) Patent No.: US 12,310,948 B2
(45) Date of Patent: *May 27, 2025

(54) APPLICATION OF MONOCYCLIC β-LACTAM COMPOUND IN PHARMACY

(71) Applicant: SHENZHEN OPTIMUM BIOLOGICAL TECHNOLOGY CO., LTD, Shenzhen (CN)

(72) Inventors: Xiawei Wei, Chengdu (CN); Charles Z. Ding, Shanghai (CN); Jian Li, Shanghai (CN); Shuhui Chen, Shanghai (CN); Yuquan Wei, Chengdu (CN)

(73) Assignee: SHENZHEN OPTIMUM BIOLOGICAL TECHNOLOGY CO., LTD, Shenzhen (CN)

( * ) Notice: Subject to any disclaimer, the term of this patent is extended or adjusted under 35 U.S.C. 154(b) by 967 days.

This patent is subject to a terminal disclaimer.

(21) Appl. No.: 17/414,491

(22) PCT Filed: Dec. 18, 2019

(86) PCT No.: PCT/CN2019/126261
§ 371 (c)(1),
(2) Date: Jun. 16, 2021

(87) PCT Pub. No.: WO2020/125670
PCT Pub. Date: Jun. 25, 2020

(65) Prior Publication Data
US 2022/0062244 A1 Mar. 3, 2022

(30) Foreign Application Priority Data
Dec. 18, 2018 (CN) .......................... 201811549551.8

(51) Int. Cl.
A61K 31/427 (2006.01)
A61K 31/04 (2006.01)
(Continued)

(52) U.S. Cl.
CPC ............ A61K 31/427 (2013.01); A61P 31/04 (2018.01)

(58) Field of Classification Search
CPC ..... A61K 31/427; A61K 31/04; C07D 417/14
See application file for complete search history.

(56) References Cited

U.S. PATENT DOCUMENTS 5,290,929 A 3/1994 Koster et al.
11,459,323 B2 10/2022 Gu et al.
(Continued)

FOREIGN PATENT DOCUMENTS

CN 106164072 A 11/2016
CN 108137573 A 6/2018
(Continued)

OTHER PUBLICATIONS

Japanese Office Action regarding Patent Application No. 2021535115, dated Jul. 19, 2022.
(Continued)

Primary Examiner — Sun Jae Yoo
(74) Attorney, Agent, or Firm — Harness, Dickey & Pierce, P.L.C.

(57) ABSTRACT

An application of a compound represented by formula (I) and pharmaceutically acceptable salts thereof in preparation of a drug for treating pneumonia.
(Continued)

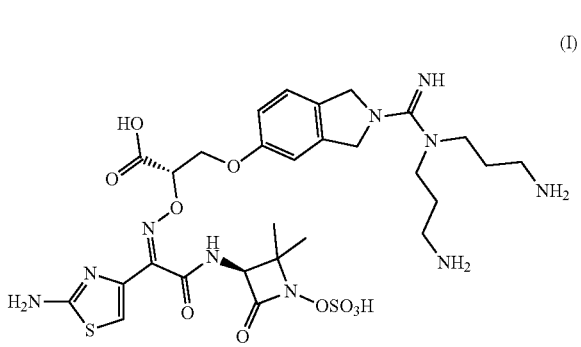

19 Claims, 1 Drawing Sheet

(51) Int. Cl.
*A61P 31/04* (2006.01)
*C07D 417/14* (2006.01)

(56) References Cited

U.S. PATENT DOCUMENTS

| 2018/0273522 | A1 | 9/2018 | Aubin et al. |
| 2021/0115035 | A1 | 4/2021 | Gu et al. |
| 2023/0022708 | A1 | 1/2023 | Wei et al. |

FOREIGN PATENT DOCUMENTS

| EP | 0484881 | A2 | 5/1992 |
| EP | 0531976 | A1 | 3/1993 |
| EP | 3747883 | A1 | 12/2020 |
| JP | 2021512866 | A | 5/2021 |
| WO | WO-0222613 | A1 | 3/2002 |
| WO | WO-2007065288 | A2 | 6/2007 |
| WO | WO-2008116813 | A2 | 10/2008 |
| WO | WO-2010070523 | A1 | 6/2010 |
| WO | WO-2013110643 | A1 | 8/2013 |
| WO | WO-2015148379 | A1 | 10/2015 |
| WO | WO-2017050218 | A1 | 3/2017 |
| WO | WO-2017155765 | A1 | 9/2017 |
| WO | WO-2018065636 | A1 | 4/2018 |
| WO | WO-2019144969 | A1 | 8/2019 |

OTHER PUBLICATIONS

Russian Office Action regarding Patent Application No. 2021121109/04(044238), dated May 27, 2022.
K.Kümmerer, Pharmaceuticals in the environment, Annual Review of Environment and Resources, 2010, V.35, p. 57-75, doi: 10.1146/annurev-environ-052809-161223.
European Search Report regarding Patent Application No. 19897972.6, dated Aug. 8, 2022.
Novikov Yu.K. Sovremennie podhodi k lecheniyu pnevmonii RMZh. 5, Mar. 5, 2002 pp. 251-254.
M.D. Mashkovsky, Lekarstvennye sredstva, Moscow, Medicina, 1993, part 1, p. 8.
Zhulenko V.N., Gorshkov G.I. Pharmacology. M.Koloss, 2008, p. 34-35.
D.A. Kharkevich Farmakologiya, 10th edition, Moscow, GEOTAR-Media, 2010, pp. 73-74.
Chuchalin_A_G_-_ Respiratornaya_meditsina_Tom_2 31-37.
Chuchalin_A_G_-_ Respiratornaya_meditsina_Tom_2 52-55.
International Search Report regarding International Application No. PCT/CN2019/126261, dated Mar. 19, 2020.
Written Opinion of the International Searching Authority regarding International Application No. PCT/CN2019/126261, dated Mar. 19, 2020.
Willyard, Cassandra, "The drug-resistant bacteria that pose the greatest health threats." Nature 543, 15 (2017).
Boucher, W., et al., "Bad Bugs, No Drugs: No ESKAPE! An Update from the Infectious Diseases Society of America." Clinical Infectious Diseases, vol. 48, Issue 1 (2009).
Sykes, R.B., et al., "Discovery and Development of the Monobactams." Reviews of Infectious Diseases, vol. 7, Issue Supplement_4 (1985), S579-S593.
Berge, Stephen M., et al., "Pharmaceutical Salts." Journal of Pharmaceutical Sciences, vol. 66, Issue 1 (1977), 1-19.
Remington, "The Science and Practice of Pharmacy." 21st edition (2006), preface and index only.
Unpublished Chinese Priority Application No. CN201811549551.8.

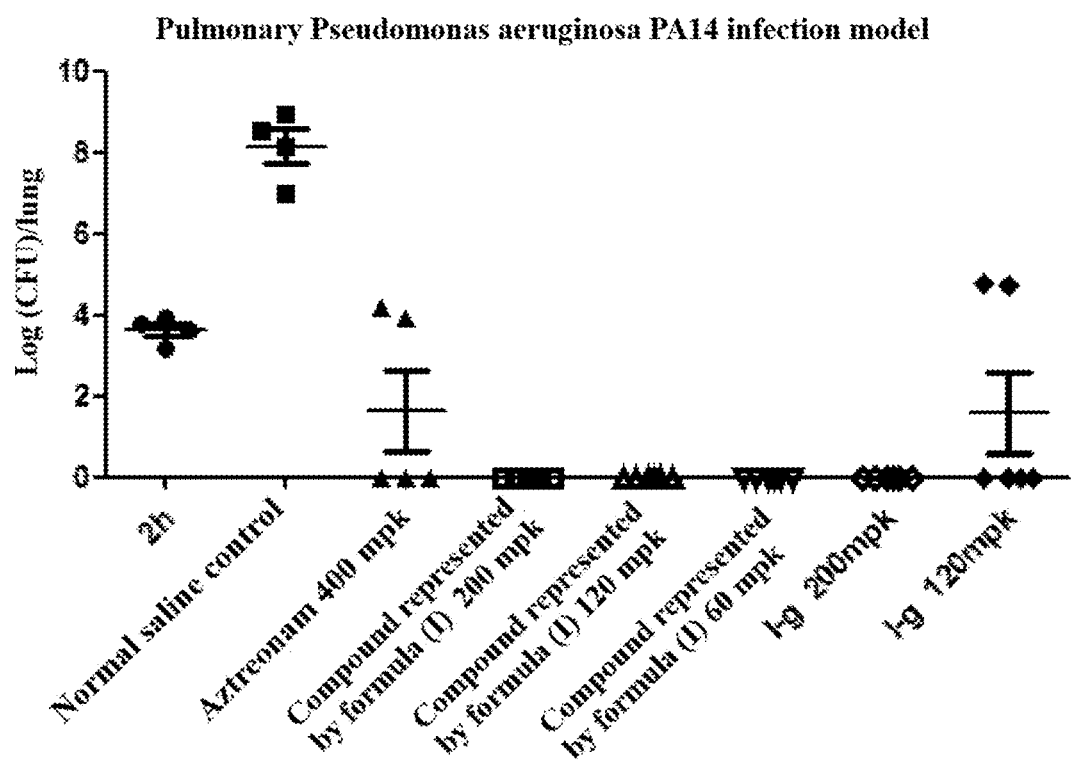

APPLICATION OF MONOCYCLIC β-LACTAM COMPOUND IN PHARMACY

CROSS-REFERENCE TO RELATED APPLICATIONS

This application is a U.S. National Phase Application under 35 U.S.C. 371 of International Application No. PCT/CN2019/126261, filed on Dec. 18, 2019, which claims the benefit of Chinese Patent Application No. 201811549551.8, filed on Dec. 18, 2018. The entire disclosures of the above applications are incorporated herein by reference.

TECHNICAL FIELD

The present invention relates to an application of a compound represented by formula (I) and pharmaceutically acceptable salts thereof in the field of pharmacy.

BACKGROUND

Public health experts and officials generally believe that the emergence and spread of drug-resistant bacteria is one of the major public health problems in the 21st century. The frequency of antibiotic resistance and its relationship with severe infectious diseases is increasing at an alarming rate. The increasing prevalence of nosocomial pathogen resistance in hospitals is particularly disturbing. Of the more than two million nosocomial infections that occur annually in the United States, 50% to 60% are caused by antibiotic-resistant bacteria. The high rate of resistance to commonly used antimicrobial agents increase the morbidity, mortality and cost associated with nosocomial infections. The number of patients who died of incurable nosocomial infections continues to increase. Antibiotic resistance kills an estimated 700,000 people each year worldwide, and some experts predict that number to reach 10 million by 2050 if efforts are not made to develop new therapeutics or therapeutic schedules (Nature, 2017, 543, 15). The treatment options available for infections caused by multidrug-resistant Gram-negative bacteria, including Enterobacteriaceae and non-fermenters, are particularly limited; even more serious, the development pipeline of the pharmaceutical industry contains few compounds that can break through the resistance of bacteria (Clin. Inf. Dis., 2009, 48, 1-12).

Over the last few decades, a very successful and well tolerated class of β-lactam antibiotics has been the primary basis for the treatment of infections caused by Gram-negative pathogens. Of these, especially the third generation cephalosporins, carbapenems and monocyclic lactams are widely used for the treatment of infections caused by Gram-negative bacteria. However, the emergence of more and more β-lactamases and other resistance mechanisms seriously endangers the mid-term availability of current compounds in these subclasses, especially extended-spectrum lactamases (ESBL) and carbapenemases are important driving force of drug resistance; therefore, there is an urgent need for new β-lactam antibiotics that can break through drug resistance to fill the gap.

As the only FDA-approved monocyclic β-lactam used worldwide and the second analogue (tigemonam) only sold in the Japanese market, the value of Aztreonam as monocyclic β-lactam antibiotics is far from being unearthed (Rev. Infect. Dis., 1985, 7, 579-593). On the other hand, bacterial resistance worsens the penetrability of aztreonam, enhances the exocytosis, and reduces the antibacterial spectrum. To increase the permeability of monocyclic β-lactams to bacteria, a series of iron carrier uptakes system were introduced on monocyclic β-lactam molecules in Basilea (WO 2007065288), Naeja Pharmaceuticals (WO 2002022613) and Squibb & Sons (MS 5290929, EP 531976, EP 484881). Recently, a monocyclic β-lactam carrying a sulfonamido carbonyl activating group at the N1-position has been re-studied by Pfizer (WO 2010070523). In addition, in WO 2008116813, Basilea describes a combination therapy using monocyclic β-lactams and carbapenems. AiCuris (WO 2013110643) and Novartis (WO 2015148379) reported studies to enhance activity by modifying substituents on Aztreonam molecules, respectively, with compounds of the formula shown below, wherein group A is an aromatic ring structure to which amidino and guanidino groups are attached. Novartis (WO 2017050218) also reports salt forms of one of the compounds, which are currently in preclinical or clinical development.

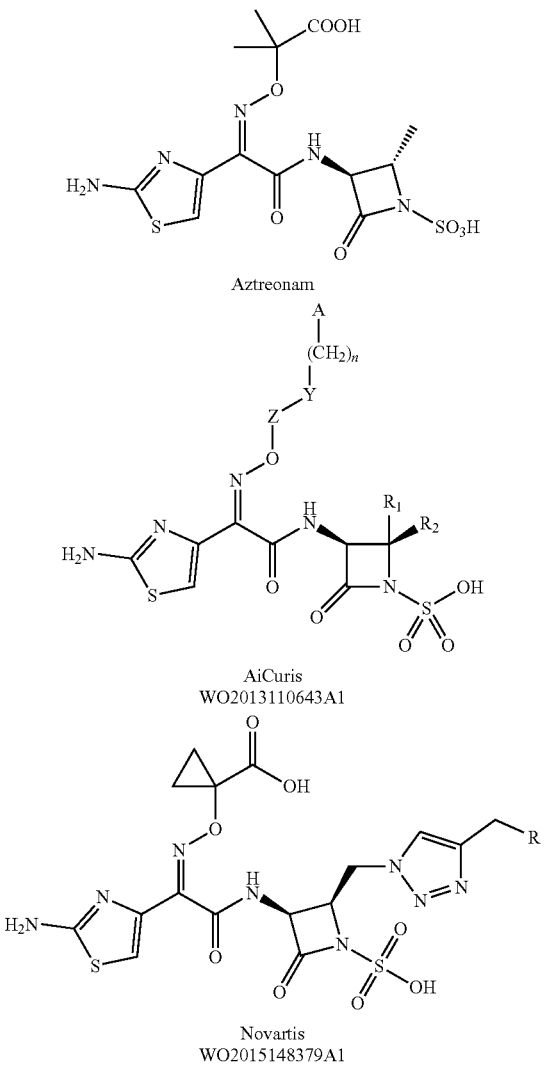

SUMMARY

The present invention provides an application of a compound represented by formula (I) or a pharmaceutically acceptable salt thereof in manufacture of a medicament for treating pneumonia.

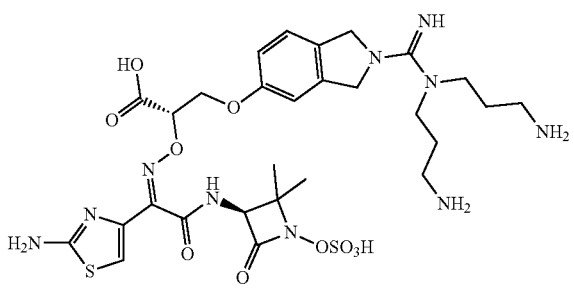

(I)

In some embodiments of the present invention, wherein the pneumonia in the application as described above is caused by infection with *Pseudomonas aeruginosa*.

The present invention also provides a pharmaceutical composition comprising a therapeutically effective amount of a compound represented by formula (I) or a pharmaceutically acceptable salt thereof as an active ingredient and one or more pharmaceutically acceptable excipients and/or pharmaceutically acceptable carriers.

In some embodiments of the present invention, wherein the excipient in the composition as described above is a surface stabilizer, a solubilizer, a buffer, an opacifier, a binder, a disintegrant, or a lubricant.

In some embodiments of the present invention, wherein the surface stabilizer in the composition as described above comprises an amphoteric surfactant, a nonionic surfactant, a cationic surfactant, or an anionic surfactant, or a combination thereof.

In some embodiments of the present invention, wherein the pharmaceutical composition in the composition as described above is for oral use.

In some embodiments of the present invention, wherein the pharmaceutical composition in the composition as described above is a tablet or a capsule.

In some embodiments of the present invention, wherein the pharmaceutical combination in the composition as described above is in the form of an injectable formulation or an inhaled formulation.

The present invention provides an application of the composition as described above in manufacture of a medicament for treating pneumonia.

In some embodiments of the present invention, wherein the pneumonia in the application of the composition as described above is caused by infection with Gram-negative bacteria.

In some embodiments of the present invention, wherein the pneumonia in the application of the composition as described above is caused by infection with *Pseudomonas aeruginosa*.

TECHNICAL EFFECT

The compound provided by the present invention has good antibacterial activity on Gram-negative bacteria, and especially has remarkable antibacterial activity on *Pseudomonas aeruginosa*.

Definition and Description

As used herein, the following terms and phrases are intended to have the following meanings, unless otherwise indicated. A particular term or phrase, unless specifically defined, should not be construed as indefinite or unclear, but rather construed in a generic sense. When trade names appear herein, they are intended to refer to their corresponding goods or their active ingredients. The term "pharmaceutically acceptable" is used herein to refer to those compounds, materials, compositions, and/or dosage forms as follows: within the scope of sound medical judgment, suitable for use in contact with the tissues of humans and animals without undue toxicity, irritation, allergic response, and/or other problems or complications, commensurate with a reasonable benefit/risk ratio.

The term "pharmaceutically acceptable salts" refers to salts of the compounds of the present invention which are prepared from the compounds having the specified substituents found in the present invention and relatively nontoxic acids or bases. When compounds of the present invention contain relatively acidic functional groups, base addition salts may be obtained by contacting the neutral form of such compounds with a sufficient amount of base in a neat solution or in a suitable inert solvent. Pharmaceutically acceptable base addition salts include sodium, potassium, calcium, ammonium, organic ammonia or magnesium salts or similar salts. When compounds of the present invention contain relatively basic functionalities, acid addition salts may be obtained by contacting the neutral form of such compounds with a sufficient amount of acid in a neat solution or in a suitable inert solvent. Examples of pharmaceutically acceptable acid addition salts include inorganic acid salts including, for example, hydrochloric acid, hydrobromic acid, nitric acid, carbonic acid, bicarbonate, phosphoric acid, monohydrogen phosphate, dihydrogen phosphate, sulfuric acid, hydrogen sulfate, hydriodic acid, phosphorous acid, and the like; and organic acid salts including acids, for example, acetic acid, propionic acid, isobutyric acid, maleic acid, malonic acid, benzoic acid, succinic acid, suberic acid, fumaric acid, lactic acid, mandelic acid, phthalic acid, benzenesulfonic acid, p-toluenesulfonic acid, citric acid, tartaric acid, methanesulfonic acid and the like; also include salts of amino acids such as arginine, as well as salts of organic acids such as glucuronic acid (see Berge et al., "Pharmaceutical Salts", Journal of Pharmaceutical Science 66:1-19 (1977)). Certain specific compounds of the present invention contain basic and acidic functional groups, thus they can be converted to any base or acid addition salt.

Preferably, a neutral form of the compound is regenerated by contacting the salt with a base or acid in a conventional manner and isolating a parent compound. The parent form of a compound differs from its various salt forms in certain physical properties, such as solubility in polar solvents.

As used herein, a "pharmaceutically acceptable salt" is a derivative of a compound of the present invention in which the parent compound is modified by salifying with an acid or with a base. Examples of pharmaceutically acceptable salts include, but are not limited to: basic group such as inorganic or organic acid salts of amines, acid radicals such as alkali or organic salts of carboxylic acids. The pharmaceutically acceptable salts include conventional non-toxic salts or quaternary ammonium salts of the parent compound, for example salts formed from non-toxic inorganic or organic acids. Conventional non-toxic salts include, but are not limited to, those derived from inorganic and organic acids selected from 2-acetoxybenzoic acid, 2-hydroxyethanesulfonic acid, acetic acid, ascorbic acid, benzenesulfonic acid, benzoic acid, bicarbonate radical, carbonic acid, citric acid, edetic acid, ethane disulfonic acid, ethane sulfonic acid, fumaric acid, glucoheptose, gluconic acid, glutamic acid, glycolic acid, hydrobromic acid, hydrochloric acid, hydriodate, hydroxy, hydroxynaphthalene, 2-hydroxyethanesulfonic acid, lactic acid, lactose, dodecylsulfonic acid, maleic acid, malic acid, mandelic acid, methanesulfonic acid, nitric acid, oxalic acid, pamoic acid, pantothenic acid, phenylacetic acid, phosphoric acid, polygalacturonic acid, propionic acid, salicylic acid, stearic acid, acetic acid, succinic acid, sulfamic acid, p-aminobenzenesulfonic acid, sulfuric acid, tannin, tartaric acid, and p-toluenesulfonic acid.

The pharmaceutically acceptable salts of the present invention may be synthesized from the parent compound containing an acid radical or a basic group by conventional chemical methods. Generally, such salts are prepared by reacting these compounds in free acid or base form with a stoichiometric amount of appropriate base or acid in water or an organic solvent or a mixture of both. Generally, nonaqueous media such as ether, ethyl acetate, ethanol, isopropanol, or acetonitrile are preferred.

In addition to salt forms, the compounds provided herein exist in the form of prodrug. Prodrugs of the compounds described herein are readily converted to the compounds of the present invention by chemical changes under physiological conditions. In addition, prodrugs can be converted to the compounds of the present invention by chemical or biochemical methods in an in vivo environment.

Certain compounds of the present invention may exist in unsolvated or solvated forms, including hydrated forms. In general, the solvated forms are equivalent to unsolvated forms and are intended to be encompassed within the scope of the present invention.

Certain compounds of the present invention may have asymmetric carbon atoms (optical centers) or double bonds. Racemates, diastereomers, geometric isomers and individual isomers are included within the scope of the present invention.

Unless otherwise indicated, the absolute configuration of a stereocenter is indicated by the wedge-shaped solid bonds ( ▰ ) and the wedge-shaped dashed bonds ( ▱ ), the wedge-shaped solid bonds ( ▰ ) or the wedge-shaped dashed bonds ( ▱ ) is indicated by the wavy lines ( ∿ ), and the relative configuration of the stereocenter is indicated by the solid line bonds ( ▰ ) and the dashed line bonds ( ▱ ). When the compounds described herein contain olefinic double bonds or other centers of geometric asymmetry, they include E, Z geometric isomers, unless otherwise specified. Similarly, all tautomeric forms are included within the scope of the present invention.

The compounds of the present invention may exist in specific geometric or stereoisomeric forms. The present invention contemplates all such compounds, including cis and trans isomers, (−)- and (+)-enantiomers, (R)- and (S)-enantiomers, diastereomers, (D)-isomers, (L)-isomers, and racemic and other mixtures thereof, such as enantiomerically or diastereomerically enriched mixtures, all such mixtures are within the scope of the present invention. Additional asymmetric carbon atoms may be present in substituents such as alkyl groups. All such isomers and mixtures thereof are included within the scope of the present invention.

Optically active (R)- and (S)-isomers as well as D and L isomers may be prepared by chiral synthesis or chiral reagents or other conventional techniques. A desired enantiomer of a compound of the present invention may be prepared by asymmetric synthesis or derivatisation be prepared by asymmetric synthesis or derivatization with chiral auxiliary agents in which the resulting diastereomeric mixture is separated and the auxiliary group is cleaved to provide the pure desired enantiomer. Alternatively, when the molecule contains a basic functional group, such as an amino group, or an acidic functional group, such as a carboxyl group, diastereomeric salts are formed with an appropriate optically active acid or base, followed by diastereomeric resolution by conventional methods well known in the art, followed by recovery to obtain pure enantiomers. In addition, the enantiomers and diastereomers are typically separated using chromatography employing a chiral stationary phase, optionally in combination with chemical derivatization (e.g., formation of carbamate from an amine).

The compound of the present invention may contain unnatural proportions of atomic isotopes on one or more of the atoms constituting the compound. For example, compounds may be labeled with radioisotopes, such as tritium ($^3$H), iodine-125 ($^{125}$I), or C-14 ($^{14}$C). All isotopic variations of the compounds of the present invention, whether radioactive or not, are included within the scope of the present invention.

The term "pharmaceutically acceptable carrier" refers to any formulation or carrier medium capable of delivering an effective amount of an active agent of the present invention without interfering with the biological activity of the active agent and without toxic or side effects to the host or patient. Representative carriers include water, oils, vegetables and minerals, creams, lotions bases, ointments bases, and the like. These include suspending agents, tackifiers, transdermal enhancers, and the like. For further information on carriers, reference may be made to Remington: The Science and Practice of Pharmacy, 21st Ed., Lippincott, Williams & Wilkins (2005), the contents of which are incorporated herein by reference.

The term "excipient" generally refers to a carrier, diluent and/or medium required to formulate an effective pharmaceutical composition.

For a drug or pharmacologically active agent, the term "effective amount" or "therapeutically effective amount" refers to an amount of the drug or agent that is nontoxic but sufficient to achieve the desired effect. For oral dosage forms of the present invention, an "effective amount" of one active substance in a composition refers to the amount required to achieve the desired effect when combined with another active substance in the composition. Determination of the effective amount will vary from person to person, depending on the age and general condition of the recipient, and also on the particular active substance, and suitable effective amounts in each case may be determined by one skilled in the art according to routine experimentation.

The terms "active ingredient", "therapeutic agent", "active substance", or "active agent" refer to a chemical entity that is effective in treating a disorder, disease, or condition of interest.

The solvents used in the present invention are commercially available.

The present invention adopts the following abbreviations: aq represents water; min represents minutes; FA represents formic acid; m-CPBA represents 3-chloroperoxybenzoic acid; eq represents an equivalent amount; DCC represents N,N'-dicyclohexylcarbodiimide; DCM represents dichloromethane; PE represents petroleum ether; DIAD represents diisopropyl azodicarboxylate; DMF represents N,N-dimethylformamide; $BH_3 \cdot SMe_2$ represents borane dimethyl sulfide; DMSO represents dimethylsulfoxide; EtOAc represents ethyl acetate; EtOH represents ethanol; MeOH represents methanol; Cbz represents benzyloxycarbonyl, an amine protecting group; Boc represents tert-butoxycarbonyl, an amine protecting group; HOAc represents acetic acid; ACN represents acetonitrile; $BH_3$ represents sodium cyanoborohydride; r. t. represents room temperature; THF represents tetrahydrofuran; $Boc_2O$ represents di-tert-butyl dicarbonate; TFA represents trifluoroacetic acid; DIPEA represents diisopropylethylamine; $SOCl_2$ represents thionyl chloride; iPrOH represents 2-propanol; mp represents melting point; LDA represents lithium diisopropylamide; TEMPO represents 2,2,6,6-tetramethylpiperidine-1-oxyl radical or 2,2,6,6-tetramethylpiperidine oxide; NaClO represents sodium hypochlorite; $NaClO_2$ represents sodium chlorite; HOBt represents 1-hydroxybenzotriazole; psi represents pounds per square inch; $DMF·SO_3$ represents N,N-dimethylformamide sulfur trioxide; $KH_2PO_4$ represents potassium dihydrogen phosphate; $Bu_4HSO_4$ represents tetrabutylammonium hydrogensulfate; $PPh_3$ represents triphenylphosphine; $NH_2NH_2·H_2O$ represents hydrazine hydrate; dppf represents 1,1'-bis (diphenylphosphino) ferrocene; $Pd_2(dba)_3$ represents tris (dibenzylideneacetone) dipalladium (0); MIC represents minimum inhibitory solubility; DMAP represents 4-dimethylaminopyridine; BnBr represents benzyl bromide; $H_2O_2$ represents hydrogen peroxide.

BRIEF DESCRIPTION OF DRAWINGS

FIG. 1 shows the results of the lung bacterial load in the treatment of pulmonary *Pseudomonas aeruginosa* infection in immunosuppressive mice.

DETAILED DESCRIPTION

The following examples describe the present invention in detail, but they are not meant to impose any unfavorable limitation on the present invention. The present invention has been described in detail herein, and its specific embodiments are also disclosed. It will be apparent to those skilled in the art that various changes and modifications can be made to the specific embodiments without departing from the spirit and scope of the present invention.

Synthesis of Intermediate A1

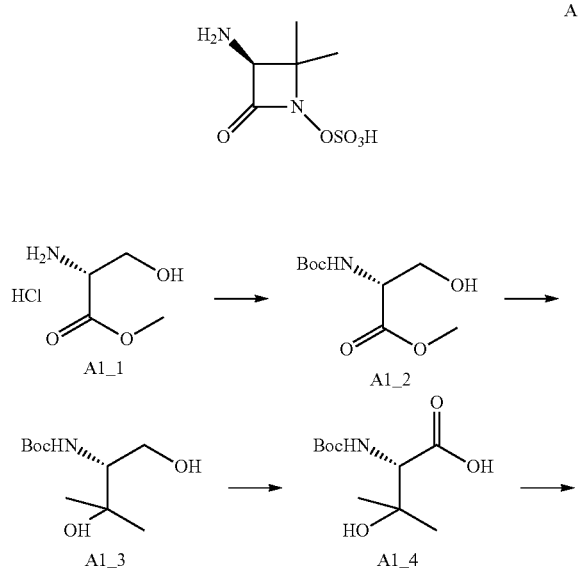

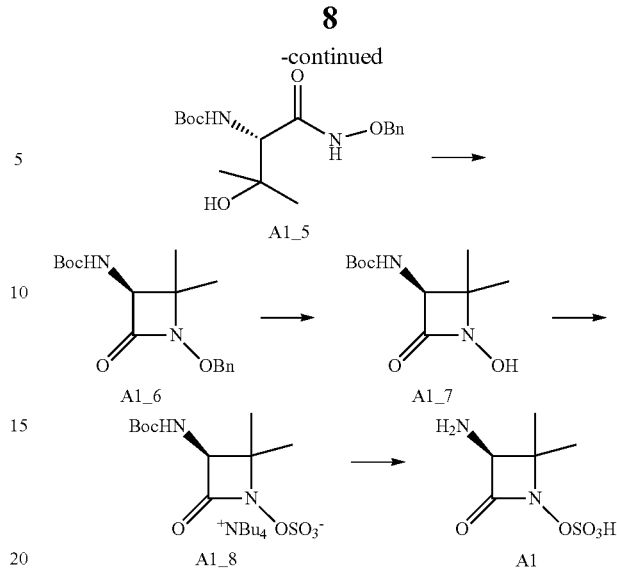

Step 1: To THF (1.50 L) were added Compound A1_1 (100.00 g, 642.76 mmol, 1.00 eq) and triethylamine (136.59 g, 1.35 mol, 187.10 mL, 2.10 eq), and the resulting mixture was cooled to 0° C.; $Boc_2O$ (154.31 g, 707.03 mmol, 162.43 mL, 1.10 eq) in THF (500.00 mL) was added dropwise at this temperature, the reaction mixture was warmed to 10° C. and stirred at this temperature for 10 h, and then filtered; the filtrate was concentrated under reduced pressure to obtain a crude product, to which saturated sodium bicarbonate solution (300 mL) was added, and the mixture was extracted with ethyl acetate (500 mL*2); the combined organic layers were dried over anhydrous sodium sulfate, filtered and concentrated under reduced pressure to obtain Compound A1_2.

$^1$H NMR (400 MHz, $CDCl_3$) δ (ppm): 5.51 (br s, 1H), 4.46-4.31 (m, 1H), 4.03-3.86 (m, 2H), 3.83-3.72 (m, 3H), 2.64 (br s, 1H), 1.46 (s, 9H).

Step 2: A1_2 was dissolved in THF (2000 mL), the mixture was stirred at −50° C. for 10 min, then MeMgBr (3M, 638.59 mL, 6.00 eq) was added dropwise over 20 min at −50° C. The resulting mixture was stirred at 25° C. for 60 min before the reaction mixture was quenched at 0° C. by the addition of dilute hydrochloric acid (2000 mL, 0.5 M), then the resulting mixture was extracted with ethyl acetate (500 mL*2); the combined organic layers were washed with saturated aqueous sodium chloride solution, dried over anhydrous sodium sulfate, and filtered, the filtrate was concentrated under reduced pressure to obtain a crude product, which was washed with petroleum ether/ethyl acetate (70 mL, 10/1) by stirring and purified by column chromatography ($SiO_2$, petroleum ether/ethyl acetate=10/1 to 1/1 (v/v)) to obtain Compound A1_3.

$^1$H NMR (400 MHz, $CDCl_3$) δ (ppm): 5.41-5.23 (m, 1H), 3.96 (br d, J=11.2 Hz, 1H), 3.79-3.70 (m, 1H), 3.40 (br d, J=8.3 Hz, 1H), 2.53-2.39 (m, 2H), 1.39 (s, 9H), 1.28 (s, 3H), 1.18 (s, 3H).

Step 3: A1_3 (30 g, 136.81 mmol, 1.00 eq) was dissolved in a mixed solution of sodium phosphate buffer (540.00 mL, 0.7 M, 2.76 eq) and acetonitrile (300 mL), then TEMPO (2.15 g, 13.68 mmol, 0.10 eq) was added, NaClO (81.47 g, 5.47 mmol, 67.33 mL, purity 0.5%, 0.04 eq) and $NaClO_2$ (98.99 g, 1.09 mol, 8.00 eq) in water (300 mL) were added dropwise by stirring at 35° C.; the resulting mixture was stirred at 35° C. for 12 h, then cooled to room temperature, and citric acid (10 g) was added; the resulting mixture was extracted with ethyl acetate (500 mL*4), the combined organic layers were washed with saturated aqueous sodium chloride solution (100 mL), dried over anhydrous sodium sulfate, and filtered, and the filtrate was concentrated under reduced pressure. To the resulting crude product was added aqueous sodium carbonate (300 mL, 2 M) and washed with ethyl acetate (200 mL*2); the aqueous layer was cooled to 0° C. and the pH was adjusted to 3.0 with dilute hydrochloric acid (1 M); the aqueous solution was saturated with sodium chloride and the resulting mixture was extracted with ethyl acetate (500 mL*4); the combined organic layers were washed with saturated aqueous sodium chloride solution (50 mL), dried over anhydrous sodium sulfate, and filtered, and the filtrate was concentrated under reduced pressure to obtain Compound A1_4.

$^1$H NMR (400 MHz, CDCl$_3$) δ (ppm): 5.42 (br d, J=7.8 Hz, 1H), 4.18 (br d, J=8.4 Hz, 1H), 1.39 (s, 9H), 1.30 (s, 3H), 1.22 (s, 3H).

Step 4: A1_4 (48 g, 205.78 mmol, 1.00 eq) was dissolved in DMF (700 mL), then DCC (84.92 g, 411.56 mmol, 83.25 mL, 2.00 eq) and HOBt (55.61 g, 411.56 mmol, 2 eq) were added, the mixture was stirred at 10° C. for 0.5 h, then O-benzylhydroxylamine hydrochloride (39.41 g, 246.93 mmol, 1.20 eq) and sodium bicarbonate (69.15 g, 823.11 mmol, 32.01 mL, 4 eq) in water were added; the resulting mixture was stirred at 10° C. for 1.5 h, then the reaction mixture was filtered and the filtrate was concentrated under reduced pressure; the crude product was diluted with water (400 mL) and extracted with ethyl acetate (500 mL*2). The combined organic layers were washed with saturated aqueous sodium chloride solution, dried over anhydrous sodium sulfate and filtered; the filtrate was concentrated under reduced pressure, and the resulting residue was purified by column chromatography (SiO$_2$, petroleum ether/ethyl acetate=6/1 to 3/1 (v/v)) to obtain Compound A1_5.

$^1$H NMR (400 MHz, DMSO-d$_6$) δ (ppm): 11.06 (s, 1H), 7.45-7.32 (m, 5H), 6.45 (br d, J=9.2 Hz, 1H), 4.80 (d, J=2.6 Hz, 2H), 4.65 (s, 1H), 4.04 (d, J=7.0 Hz, 1H), 3.77 (br d, J=9.2 Hz, 1H), 1.40 (s, 9H), 1.11 (s, 3H), 1.08 (s, 3H);

LC-MS (ESI) m/z: 283 (M−56+1).

Step 5: A1_5 (57 g, 168.44 mmol, 1 eq) was dissolved in pyridine (600 mL) by stirring at 55° C. for 12 h, and sulfur trioxide pyridine (187.67 g, 1.18 mol, 7 eq) was added; the reaction mixture was then concentrated under reduced pressure and the resulting solid was dissolved in ethyl acetate (800 mL); to the solid was added aqueous potassium carbonate (816.94 mL, 2 M, 9.7 eq) dropwise at 0° C. and the resulting mixture was stirred at 100° C. for 2 h; the reaction mixture was then cooled to room temperature and extracted with ethyl acetate (400 mL*3); the combined organic layers were dried over sodium sulfate, filtered and concentrated under reduced pressure; the resulting crude product was purified by column chromatography (SiO$_2$, petroleum ether/ethyl acetate=12/1 to 9/1 (v/v)) to obtain Compound A1_6.

$^1$H NMR (400 MHz, CDCl$_3$) δ (ppm): 7.41 (br d, J=1.0 Hz, 5H), 5.02-4.97 (m, 2H), 4.32 (d, J=6.7 Hz, 1H), 1.50-1.43 (m, 9H), 1.34 (s, 3H), 1.11 (s, 3H);

LC-MS (ESI) m/z: 321.1 (M+1).

Step 6: A1_6 (31 g, 96.76 mmol, 1.00 eq) was dissolved in methanol (620 mL) and Pd/C (3 g, 10%) was added under a nitrogen atmosphere, then the reaction vial was replaced with nitrogen three times, then the reaction vial was charged with hydrogen gas at 20° C. and reacted under 50 psi atmosphere for 1 h, then the reaction mixture was filtered and the filtrate was concentrated under reduced pressure to obtain Compound A1_7.

Step 7: to a solution of A1_7 (22 g, 95.54 mmol, 1.00 eq) in DMF (220 mL) was added DMF·SO$_3$ (17.56 g, 114.65 mmol, 1.2 eq); the mixture was stirred at 0° C. for 1 h and then diluted with saturated KH$_2$PO$_4$ (200 mL); the resulting mixture was extracted with ethyl acetate (100 mL), and Bu$_4$HSO$_4$ (38.93 g, 114.65 mmol, 1.20 eq) was added to the combined aqueous layers over 20 min at 10° C., and the resulting aqueous phase was extracted with EtOAc (350 mL*4); the combined organic phases were concentrated under reduced pressure to obtain Compound A1_8.

Step 8: A1_8 (68 g, 123.24 mmol, 1.00 eq) was added to trifluoroacetic acid (300 mL) and the mixture was stirred at 15° C. for 4 h under a nitrogen atmosphere; the reaction mixture was diluted with dichloromethane (350 mL) and filtered, and the filtrate was concentrated under reduced pressure to obtain Compound A1.

$^1$H NMR (400 MHz, DMSO-d$_6$) δ (ppm): 8.79 (br s, 3H), 4.18 (br s, 1H), 1.46-1.38 (m, 6H).

Synthesis of Intermediate A2

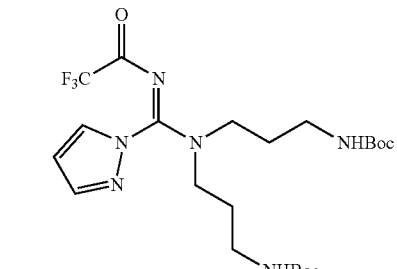

A2

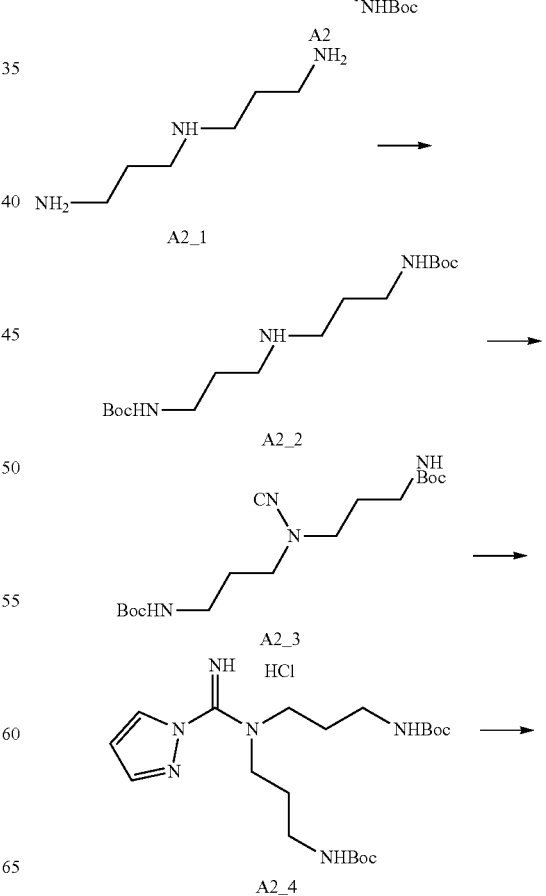

-continued

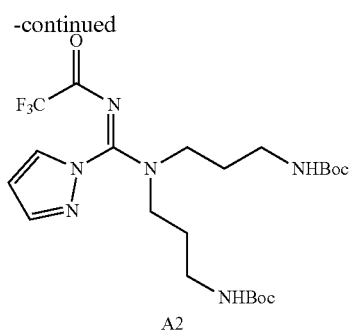

A2

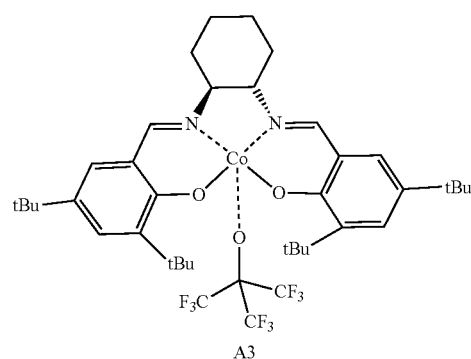

A3_1

Step 1: to a solution of A2_1 (7 g, 53.35 mmol, 7.54 mL, 1 eq) in THF (70 mL) was slowly dropwise added BOC-ONB (29.80 g, 106.69 mmol, 2 eq) and Et₃N (11.34 g, 112.03 mmol, 15.59 mL, 2.1 eq) in THF (330 mL) at 20° C., and the resulting mixture was stirred at 20° C. for 11 h, filtered and the filtrate was concentrated under reduced pressure, the resulting residue was diluted with potassium carbonate solution (100 mL, 2 M) and extracted with ethyl acetate (100 mL*2); the organic phases were combined and concentrated under reduced pressure to obtain Compound A2_2.

Step 2: to a solution of A2_2 (15 g, 45.26 mmol, 1 eq) in MeOH (150 mL) was added BrCN (7.86 g, 74.21 mmol, 5.46 mL, 1.64 eq) and sodium acetate (7.43 g, 90.51 mmol, 2 eq) at 0° C., the mixture was stirred at room temperature for 2 h, then diluted with a saturated sodium carbonate solution (300 mL) and extracted with ethyl acetate (100 mL); the organic phases were concentrated under reduced pressure, and the residue was purified by column chromatography (SiO₂, petroleum ether/ethyl acetate=5/1 to 1/1) to obtain Compound A2_3.

Step 3: Compound A2_3 (4.2 g, 11.78 mmol, 1 eq) and pyrazole hydrochloride (1.23 g, 11.78 mmol, 1 eq) were added to THF (40 mL) and replaced with nitrogen three times, then the mixture was stirred at 75° C. for 12 h; the reaction was cooled to room temperature, diluted with ethyl acetate (100 mL), filtered and the filter cake was collected to obtain Compound A2_4 after drying.

LCMS (ESI) m/z: 425.4 (M+1).

Step 4: to a solution of Compound A2_4 (2.1 g, 4.56 mmol, 1 eq) in DCM (20 mL) at 0° C. was added TFAA (765.41 mg, 3.64 mmol, 506.89 μL, 0.8 eq) and triethylamine (1.01 g, 10.02 mmol, 1.39 mL, 2.2 eq), the mixture was stirred at 0° C. for 20 min then diluted with water (20 mL), the resulting mixture was extracted with DCM (50 mL*2), the organic layers were combined and concentrated under reduced pressure to obtain Compound A2.

Synthesis of Intermediate A3

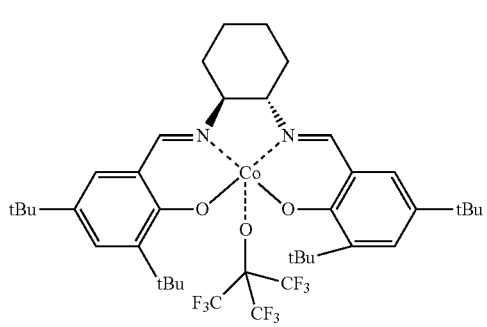

A3

Step 1: Compound A3_1 was added to a mixed solution of 1,1,1,3,3,3-hexafluoro-2-(trifluoromethyl) propan-2-ol (10.16 g, 43.06 mmol, 10 eq) and DCM (20 mL), the reactant was stirred at room temperature for 45 min (20-25° C.) and concentrated under reduced pressure to obtain Compound A3.

Example 1: Preparation of a Compound Represented by Formula (I)

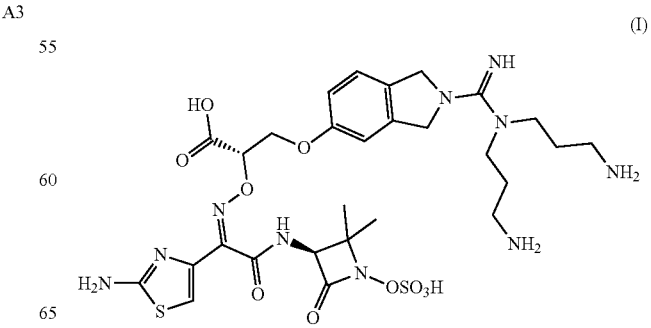

(I)

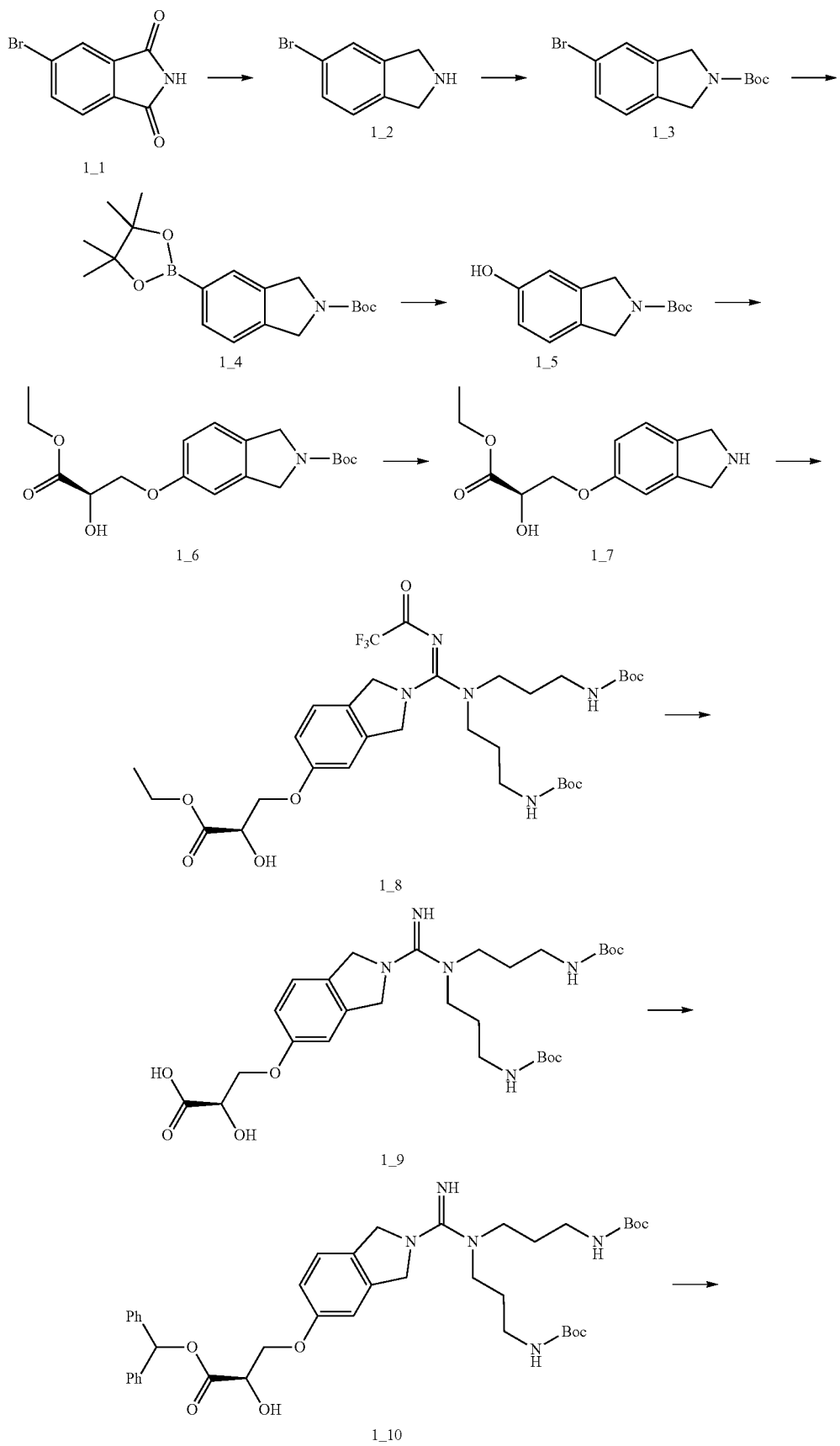

-continued
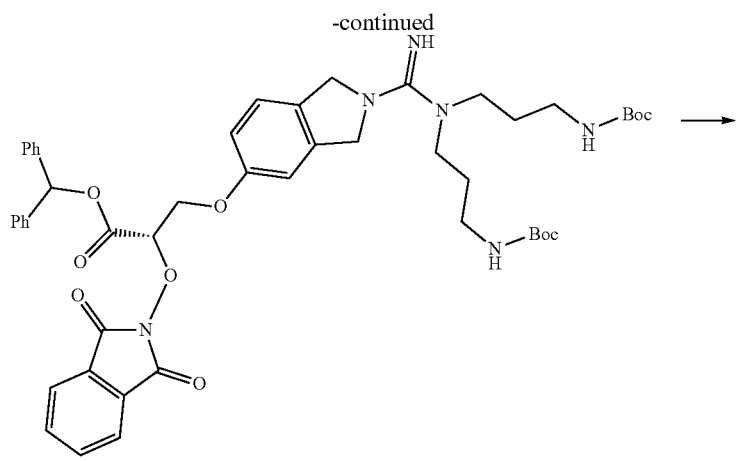
1_11
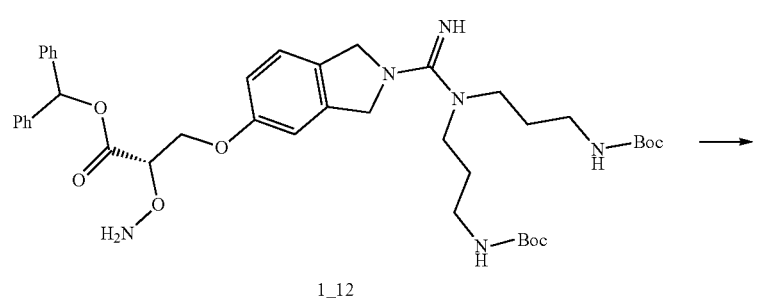
1_12
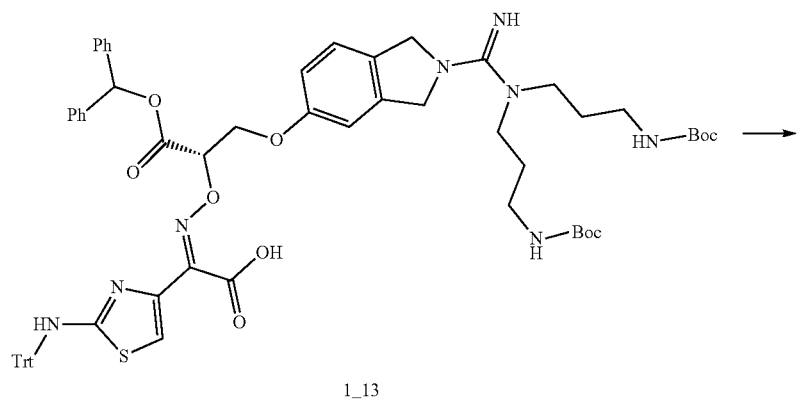
1_13
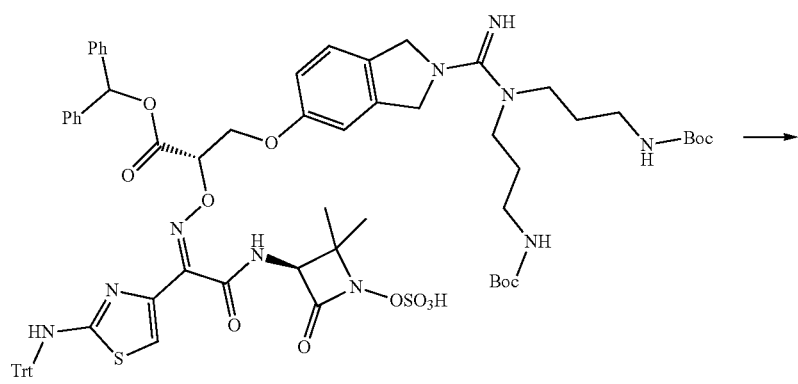
1_14

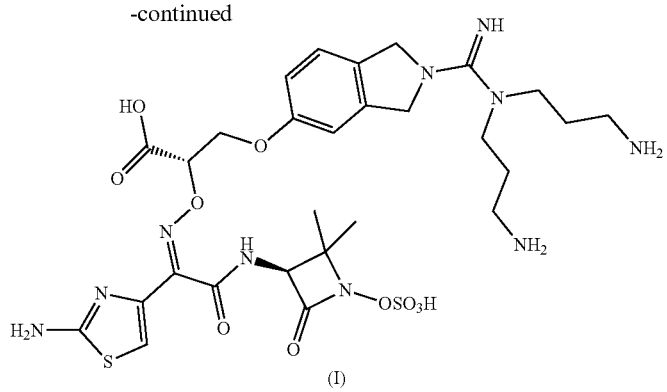

(I)

Step 1: to a solution of compound 1_1 (29 g, 128.30 mmol, 1 eq) in THF (300 mL) was added BH$_3$·SMe$_2$ (10 M, 38.49 mL, 3 eq). The mixture was reacted at 80° C. for 12 h, then cooled to 0° C., and quenched with methanol (100 mL); diluted hydrochloric acid (90 mL, 1 M) was then added by stirring at 80° C. for 1 h, and the mixture was concentrated under reduced pressure to remove the solvent; the residue was diluted with water (100 mL) and extracted with ethyl acetate (150 mL*2); the aqueous layer was then adjusted to pH=10-11 with aqueous sodium hydroxide (1 M) and the resulting aqueous phase was extracted with ethyl acetate (150 mL*2); the combined organic layers were dried over anhydrous sodium sulfate, filtered and concentrated under reduced pressure to obtain Compound 1_2.

Step 2: to a solution of compound 1_2 (6 g, 30.29 mmol, 1 eq) in dichloromethane (50 mL) was added Boc$_2$O (6.61 g, 30.29 mmol, 6.96 mL, 1 eq) and triethylamine (6.13 g, 60.59 mmol, 8.43 mL, 2 eq); the mixture was stirred at 20° C. for 12 h and concentrated under reduced pressure to remove the solvent; the residue was diluted with water (100 mL) and extracted with ethyl acetate (50 mL*3); the combined organic layers were concentrated under reduced pressure to obtain a residue, which was purified by column chromatography (SiO$_2$, petroleum ether/ethyl acetate=1/0 to 10/1 (v/v)) to obtain Compound 1_3.

Step 3: to Compound 1_3 (9 g, 30.18 mmol, 1 eq) and 4,4,4',4',5,5,5',5'-octamethyl-2,2'-bis (1,3,2-dioxaborane) (15.33 g, 60.37 mmol, 2 eq) in DMSO (150 mL) was added Pd(dppf)Cl$_2$·CH$_2$Cl$_2$ (2.46 g, 3.02 mmol, 0.1 eq) and potassium acetate (11.85 g, 120.73 mmol, 4 eq); the mixture was replaced with nitrogen three times and stirred at 90° C. for 12 h; the reaction mixture was diluted with water (200 mL) and extracted with ethyl acetate (150 mL*3); the combined organic layers were filtered and the filtrate was concentrated under reduced pressure, and the residue was purified by column chromatography (SiO$_2$, petroleum ether/ethyl acetate=100/1 to 20/1 (v/v)) to obtain Compound 1_4.

Step 4: to a solution of Compound 1_4 (11 g, 31.86 mmol, 1 eq) in THF (100 mL) was added H$_2$O$_2$ (86.69 g, 764.69 mmol, 73.47 mL, purity 30%, 24 eq) and acetic acid (9.95 g, 165.68 mmol, 9.48 mL, 5.2 eq); the mixture was stirred at 20° C. for 12 h, then quenched with saturated sodium carbonate (30 mL), and the resulting mixture was diluted with water (10 mL) and extracted with ethyl acetate (20 mL*2); the combined organic layers were concentrated under reduced pressure to obtain a residue, which was purified by column chromatography (SiO$_2$, petroleum ether/ethyl acetate=15/1 to 7/1 (v/v)) to obtain Compound 1_5. LC-MS (ESI) m/z: 180 (M−56+1). $^1$H NMR (400 MHz, DMSO-d$_6$) δ(ppm): 7.09 (t, J=6.3 Hz, 1H), 6.72-6.65 (m, 2H), 4.47 (br t, J=12.7 Hz, 4H), 1.45 (s, 9H).

Step 5: to a solution of Intermediate 1_5 (6.8 g, 26.69 mmol, 1 eq), ethyl oxirane-2-carboxylate (7.75 g, 66.72 mmol, 2.5 eq), and 4 Å molecular sieves (8 g) in MTBE (10 mL) was added Catalyst A3 (673.34 mg, 800.64 μmol, 0.03 eq), the mixture was replaced with nitrogen three times and stirred at 20° C. for 12 h; the reaction mixture was diluted with ethyl acetate (30 mL), filtered and the filtrate was concentrated under reduced pressure and purified by column chromatography (SiO$_2$, petroleum ether/ethyl acetate=6/1 to 3/1 (v/v)) to obtain Compound 1_6.

Step 6: to a solution of compound 1_6 (6.3 g, 17.32 mmol, 1 eq) in DCM (20 mL) was added TFA (14.88 g, 130.51 mmol, 9.66 mL, 7.53 eq) at 0° C., the mixture was stirred at 20° C. for 1 h and concentrated under reduced pressure to obtain trifluoroacetic acid salt of Compound 1_7.

Step 7: to a solution of Intermediate A2 (3.8 g, 7.30 mmol, 1 eq) in DMF (30 mL) was added triethylamine (2.95 g, 29.20 mmol, 4.06 mL, 4 eq) and trifluoroacetic acid salt of Compound 1_7 (5.33 g, 14.60 mmol, 2 eq); the mixture was stirred at 45° C. for 2 h, then concentrated under reduced pressure to remove DMF, the residue was diluted with water (50 mL) and extracted with ethyl acetate (50 mL); the combined organic layers were washed with saturated aqueous sodium chloride solution (25 mL), dried over anhydrous sodium sulfate, filtered and concentrated under reduced pressure to obtain a residue, which was purified by column chromatography (SiO$_2$, petroleum ether/ethyl acetate=1/1 to 0/1) to obtain Compound 1_8. LCMS (ESI) m/z: 704.4 (M+1).

Step 8: to a solution of Compound 1_8 (3.3 g, 4.50 mmol, 1 eq) in MeOH (20 mL) was added NaOH (378.39 mg, 9.46 mmol, 2.1 eq); after the mixture was stirred at 20° C. for 17 h, the reaction mixture was adjusted to pH=3-4 with dilute hydrochloric acid (2 M), and concentrated under reduced pressure, the residue was diluted with methanol (20 mL) to dissolve, then filtered and concentrated under reduced pressure to obtain Compound 1_9. LCMS (ESI) m/z: 580.5 (M+1).

Step 9: to a solution of Compound 1_9 (2 g, 3.45 mmol, 1 eq) in MeOH (20 mL) was added diphenyldiazomethane (1.34 g, 6.90 mmol, 2 eq); the mixture was stirred at 20° C. for 12 h, then concentrated under reduced pressure and the residue was diluted with water (20 mL) and extracted with DCM (40 mL); the combined organic layers were washed with saturated aqueous sodium chloride solution (10 mL), dried over anhydrous sodium sulfate, then filtered and concentrated under reduced pressure, and the residue was purified by column chromatography (SiO$_2$, DCM/MeOH=20/1 to 10/1 (v/v)) to obtain Compound 1_10. LCMS (ESI) m/z: 746.5 (M+1).

Step 10: to a solution of Compound 1_10 (1.2 g, 1.42 mmol, 1 eq) and 2-hydroxyisoindoline-1,3-dione (278.65 mg, 1.71 mmol, 1.2 eq) in THF (12 mL) was added PPh$_3$ (560.04 mg, 2.14 mmol, 1.5 eq) and DIAD (431.75 mg, 2.14 mmol, 415.15 µL, 1.5 eq) at 0° C.; the mixture was stirred at 20° C. for 1 h, then concentrated under reduced pressure to remove THF, and the residue was purified by column chromatography (SiO$_2$, DCM/EtOH=20/1 to 10/1 (v/v)) to obtain Compound 1_11. LCMS (ESI) m/z: 891.5 (M+1).

Step 11: to a solution of Compound 1_11 (1 g, 1.10 mmol, 1 eq) in EtOH (10 mL) was added NH$_2$NH$_2$·H$_2$O (77.95 mg, 1.32 mmol, 75.68 µL, purity 85%, 1.2 eq); the mixture was stirred at 20° C. for 30 min, filtered and the filtrate was concentrated under reduced pressure, the residue was diluted with water (10 mL) and extracted with DCM (20 mL), the combined organic layers were dried over anhydrous ammonium sulfate, filtered and concentrated under reduced pressure to obtain Compound 1_12. LCMS (ESI) m/z: 761.5 (M+1).

Step 12: to a solution of compound 1_12 (900 mg, 1.00 mmol, 1 eq) in DCM (5 mL) and EtOH (5 mL) was added intermediate A 2 (416.01 mg, 1.00 mmol, 1 eq), the mixture was stirred under nitrogen at 20° C. for 1 h, then the reaction mixture was concentrated under reduced pressure and the residue was purified by column chromatography (SiO$_2$, DCM/MeOH=20/1 to 10/1 (v/v)) to obtain Compound 1_13. LCMS (ESI) m/z: 1157.7 (M+1).

Step 13: to a solution of Compound 1_13 (200 mg, 163.39 µmol, 1 eq) in DMF (2 mL) was added N,N-diisopropylcarbodiimide (41.24 mg, 326.77 µmol, 2 eq) and HOBt (44.15 mg, 326.77 µmol, 2 eq); after the mixture was stirred at 20° C. for 1 h, Intermediate A1 (48.08 mg, 228.74 µmol, 1.4 eq) and NaHCO$_3$ (54.90 mg, 653.55 µmol, 25.42 µL, 4 eq) were added and stirred at 20° C. for 11 h; the reaction mixture was diluted with water (8 mL), and the solid was collected by filtration to obtain Compound 1_14. LCMS (ESI) m/z: 1350.2 (M+1).

Step 14: to a solution of Compound 1_14 (220 mg, 163.01 µmol, 1 eq) in DCM (1 mL) was added TFA (1.54 g, 13.51 mmol, 1 mL, 82.85 eq) at 0° C. and stirred for 1 h; the reaction mixture was diluted with petroleum ether/ethyl acetate (10 mL, 4/1) and the solid was collected by filtration and purified by preparative HPLC (TFA, column: Phenomenex Synergi C18 150 mm×25 mm×10 µm; mobile phase: [water (0.1% TFA)-acetonitrile]; acetonitrile %: 1%-30%, 9 min) to obtain Compound (I).

$^1$H NMR (400 MHz, D$_2$O) δ=7.23 (d, J=8.4 Hz, 1H), 7.10 (s, 1H), 6.93-6.85 (m, 2H), 5.19 (dd, J=2.0, 5.7 Hz, 1H), 4.87-4.76 (m, 4H), 4.64 (s, 1H), 4.54-4.48 (m, 1H), 4.44-4.37 (m, 1H), 3.43 (br t, J=7.3 Hz, 4H), 3.04-2.91 (m, 4H), 1.98 (quin, J=7.6 Hz, 4H), 1.41 (s, 3H), 0.97 (s, 3H) ppm; LCMS (ESI) m/z: 741.3 (M+1).

Experimental Example 1: Experiment of Compound Represented by Formula (I) on Pulmonary *Pseudomonas aeruginosa* Infection in Mice 1. Experimental Strains

*Pseudomonas aeruginosa* PA14.

2. Test Drugs (1) Test compound: A compound represented by formula (I),
(2) Reference compound: AiCuris patent WO 2018065636 reference compound I-g, aztreonam (product of Dalian Meilunbio Biotechnology Co., Ltd.).

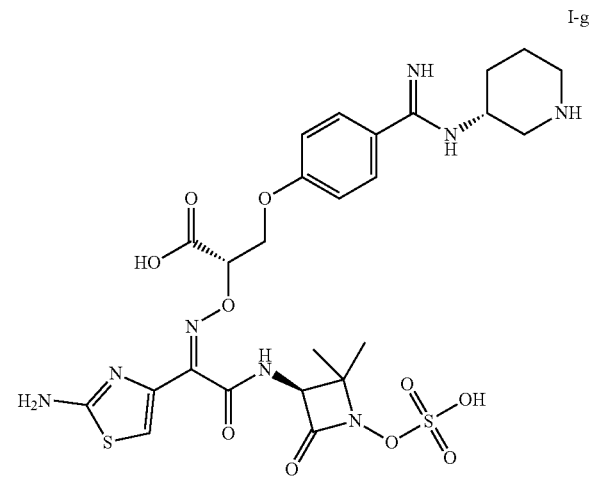 [SMILES: CC1(C)[C@H](NC(=O)/C(=N\O[C@@H](COc2ccc(C(=N)N[C@@H]3CCCNC3)cc2)C(=O)O)c2csc(N)n2)C(=O)N1OS(=O)(=O)O]

I-g

3. Medium

Mueller-Hinton agar (MHA) and TSA medium were purchased from BD.

4. Experimental Animals 46 female CD-1 (ICR) mice, supplied by Beijing Vital River Laboratory Animal Technology Co., Ltd., body weight of 23-27 g, 7 weeks old.

5. Experimental Method (1) Immunosuppressive Mice Induced by Intraperitoneal Injection of Cyclophosphamide 46 immunosuppressive mice were formed by intraperitoneal injection of cyclophosphamide 150 mg/kg on day 1 and day 4.

(2) Grouping in Experiments

Seven groups were set up, including high, medium and low dose groups of compound represented by formula (I), high and medium-dose groups of compound I-g, aztreonam group and model group; there were 6 animals in each group, the other 4 animals were subjected to pulmonary infection for 2 h, and the lung tissues were removed to count the bacterial load. See the table below for specific grouping.

TABLE 1

Experimental groups of pulmonary *Pseudomonas aeruginosa* infection in mice

| Groups | Drugs | Dose (mg/kg · day) | Mode of administration | Number of Animals |
|---|---|---|---|---|
| High-dose group of compound represented by formula (I) | Compound represented by formula (I) | 200 | 2 h, 4 h, 6 h, 8 h; ip | 6 |
| Medium-dose group of compound represented by formula (I) | Compound represented by formula (I) | 120 | 2 h, 4 h, 6 h, 8 h; ip | 6 |
| Low-dose group of compound represented by formula (I) | Compound represented by formula (I) | 60 | 2 h, 4 h, 6 h, 8 h; ip | 6 |
| High-dose group of compound I-g | I-g | 200 | 2 h, 4 h, 6 h, 8 h; ip | 6 |
| Medium-dose group of compound I-g | I-g | 120 | 2 h, 4 h, 6 h, 8 h; ip | 6 |
| Aztreonan group | Aztreonam | 400 | 2 h, 4 h, 6 h, 8 h; ip | 6 |
| Model Group | Normal saline (NS) | — | 2 h, 4 h, 6 h, 8 h; ip | 10 | each administration group were diluted 10-fold; the serial diluents were plated onto TSA plates with a spiral coater, and incubated overnight at 37° C. to determine CFU counts with a colony counter.

(6) Body Weight

The mice were weighed each day after the start of the test and body weight changes were recorded.

(7) Data Processing

CFU scatter plots of lung tissue were made using Graphpad Prism mapping software. The average CFU and body weight were calculated by SPSS 19.0 software, and the differences between groups were analyzed by variance analysis.

6. Experimental Results (1) Bacterial Load in Immunosuppressed Mice after Pulmonary Infection with *Pseudomonas aeruginosa*

Four immunosuppressed mice injected with cyclophosphamide twice intraperitoneally were infected with *Pseudomonas aeruginosa* PA14 about $1.06 \times 10^4$ CFU; after 2 h, the lung tissues were removed and homogenated to determine bacteria counting; bacterial load in mice was calculated, with average load ranging from $5.10 \times 10^3$ CFU.

(2) Body Weight Changes: The Body Weights of Each Group of Animals are Shown in Table 2.

TABLE 2

Changes of animal body weight in new monocyclic lactam antibiotics in vivo protection test

| Groups | Number of Animals (individual) | Weight on day 1 (g) | Weight on day 4 (g) | Weight on day 5 (g) |
|---|---|---|---|---|
| Model Group | 10 | 27.01 ± 1.37 | 26.25 ± 2.43 | 26.19 ± 2.43 |
| High-dose group of compound represented by formula (I) | 6 | 26.91 ± 1.03 | 28.03 ± 2.15 | 25.40 ± 2.75 |
| Medium-dose group of compound represented by formula (I) | 6 | 26.47 ± 1.65 | 28.33 ± 1.14 | 28.01 ± 1.35 |
| Low-dose group of compound represented by formula (I) | 6 | 26.14 ± 1.21 | 27.76 ± 0.43 | 26.77 ± 1.02 |
| High-dose group of compound I-g | 6 | 27.25 ± 1.14 | 28.39 ± 1.60 | 26.43 ± 1.06 |
| Medium-dose group of compound I-g | 6 | 27.02 ± 1.12 | 28.21 ± 1.16 | 27.20 ± 0.96 |
| Aztreonan group | 6 | 27.16 ± 1.74 | 27.80 ± 2.37 | 28.02 ± 1.08 |

(3) Pulmonary Infection with *Pseudomonas aeruginosa*

Mice were injected intratracheally with 50 μL of bacterial fluid ($2 \times 10^3$ CFU). Four model mice were sacrificed 2 h after infection.

(4) Administration 2 h after infection, the mice were injected intraperitoneally once at 2 h, 4 h, 6 h and 8 h according to the groups, for a total of 4 times.

(5) Bacteria Counting 24 h after infection, the mice in each group were sacrificed by cervical dislocation, and the lung and kidney tissues were removed aseptically, then placed into sterilized homogenate tube, weighed, added with proper amount of normal saline (NS), and homogenized by a homogenizer for 1 min; the lung tissues in model group were diluted $10^4$, $10^5$, and $10^6$-fold, the lung tissues in each administration group were diluted 10 and 100-fold, the kidney tissues in model group were diluted $10^2$, $10^3$, and $10^4$-fold, and the lung tissues in (3) Bacterial Load in Lung Tissue of Mice after Drug Treatment Mice were injected intraperitoneally with compounds of formula (I), compound I-g and aztreonam at 2 h, 4 h, 6 h and 8 h after infection; animals were sacrificed at 24 h, lung tissues were removed aseptically, immersed in normal saline (NS), homogenized, diluted appropriately, and then 50 μL of diluents were evenly plated onto TSA plates; the plates were incubated overnight in a 37° C. incubator to count the number of colonies, which was converted to CFU per milliliter by a dilution ratio, and logarithmic value of the bacterial load was calculated of base 10, and the mean and standard deviation were compared in each group. The results were shown in Table 3 and FIG. 1. The bacterial load at 24 h in the model group increased from $1.06 \times 10^4$ CFU to $3.34 \times 10^8$ CFU ($LOG_{10}$ of the bacterial load was 8.14). The bacterial load of each administration group was significantly lower than that of the model group, and was basically eliminated. The compound represented by formula (I) was completely eliminated in the high, middle and low-dose groups.

CONCLUSIONS

The compound represented by formula (I) has in vivo curative effect on pulmonary Pseudomonas aeruginosa infection in immunosuppressed mice caused by cyclophosphamide, and may remarkably reduce the bacterial load of lung tissues and eliminate Pseudomonas aeruginosa infected on the lung. Wherein the compound represented by formula (I) completely eliminated the bacteria infected on the lung at the lowest dose. The body weight of the animals in the administration group was not significantly changed, indicating that the compound represented by formula (I) is safe.

TABLE 3

Bacterial load of lung in immunosuppressed mice of Pseudomonas aeruginosa infection after administration treatment

| Groups | Drugs | Total Dose (mg/kg, day) | Number of Animals (individual) | $LOG_{10}$ of Bacterial load |
|---|---|---|---|---|
| Model Group | — | — | 4 | 8.14 ± 0.85 |
| High-dose group of compound represented by formula (I) | Compound represented by formula (I) | 200 | 6 | 0** |
| Medium-dose group of compound represented by formula (I) | | 120 | 6 | 0** |
| Low-dose group of compound represented by formula (I) | | 60 | 6 | 0** |
| High-dose group of compound I-g | Compound I-g | 200 | 6 | 0** |
| Medium-dose group of compound I-g | | 120 | 6 | 1.58 ± 2.45** |
| Aztreonan group | Aztreonam | 400 | 5 | 1.62 ± 2.22** |

Note:
**p < 0.01 compared to model group with very significant difference.

What is claimed is:

1. A method for treating pneumonia in a subject in need thereof, comprising administering a compound represented by formula (I) or a pharmaceutically acceptable salt thereof to the subject;

(I)

2. The method for treating pneumonia according to claim 1, wherein the pneumonia is caused by infection with Pseudomonas aeruginosa.

3. A pharmaceutical composition for treating pneumonia, comprising a therapeutically effective amount of a compound represented by formula (I) or a pharmaceutically acceptable salt thereof as an active ingredient and one or more pharmaceutically acceptable excipients and/or pharmaceutically acceptable carriers;

(I)

4. The composition according to claim 3, wherein the excipient is a surface stabilizer, a solubilizer, a buffer, an opacifier, a binder, a disintegrant, or a lubricant.

5. The composition according to claim 4, wherein the surface stabilizer comprises an amphoteric surfactant, a nonionic surfactant, a cationic surfactant, an anionic surfactant, or a combination thereof.

6. The composition according to claim 3, wherein the pharmaceutical composition is for oral use.

7. The composition according to claim 6, wherein the pharmaceutical composition is a tablet or a capsule.

8. The composition according to claim 3, wherein the pharmaceutical combination is in the form of an injection preparation or an inhalation preparation.

9. A method for treating pneumonia in a subject in need thereof, comprising administering the composition according to claim 3 to the subject.

10. The method for treating pneumonia according to claim 9, wherein the pneumonia is caused by infection with Pseudomonas aeruginosa.

11. The composition according to claim 4, wherein the pharmaceutical composition is for oral use.

12. The composition according to claim 5, wherein the pharmaceutical composition is for oral use.

13. The composition according to claim 4, wherein the pharmaceutical combination is in the form of an injection preparation or an inhalation preparation.

14. The composition according to claim 5, wherein the pharmaceutical combination is in the form of an injection preparation or an inhalation preparation.

15. A method for treating pneumonia in a subject in need thereof, comprising administering the composition according to claim 4 to the subject.

16. A method for treating pneumonia in a subject in need thereof, comprising administering the composition according to claim 5 to the subject.

17. A method for treating pneumonia in a subject in need thereof, comprising administering the composition according to claim 6 to the subject.

18. A method for treating pneumonia in a subject in need thereof, comprising administering the composition according to claim 7 to the subject.

19. A method for treating pneumonia in a subject in need thereof, comprising administering the composition according to claim 8 to the subject.

* * * * *